US012383764B2

(12) United States Patent
Krieger et al.

(10) Patent No.: US 12,383,764 B2
(45) Date of Patent: Aug. 12, 2025

(54) ENERGY TREATMENT PLAN QUALITY ASSURANCE DOSE RATE METRIC APPARATUS AND METHOD

(71) Applicant: Siemens Healthineers International AG, Steinhausen (CH)

(72) Inventors: Miriam Krieger, Halle (DE); Sylvie Spiessens, Desselgem (BE); Michael Matthew Folkerts, Costa Mesa, CA (US)

(73) Assignee: Siemens Healthineers International AG, Steinhausen (CH)

( * ) Notice: Subject to any disclaimer, the term of this patent is extended or adjusted under 35 U.S.C. 154(b) by 378 days.

(21) Appl. No.: 18/085,934

(22) Filed: Dec. 21, 2022

(65) Prior Publication Data

US 2024/0207642 A1  Jun. 27, 2024

(51) Int. Cl.
*A61N 5/10* (2006.01)

(52) U.S. Cl.
CPC .......... *A61N 5/1031* (2013.01); *A61N 5/103* (2013.01); *A61N 5/1064* (2013.01); *A61N 5/1071* (2013.01); *A61N 5/1081* (2013.01); *A61N 2005/1087* (2013.01); *A61N 2005/1089* (2013.01)

(58) Field of Classification Search
CPC .... A61N 5/103; A61N 5/1031; A61N 5/1064; A61N 5/1071; A61N 5/1081; A61N 2005/1087; A61N 2005/1089
See application file for complete search history.

(56) References Cited

U.S. PATENT DOCUMENTS

| 2017/0091387 | A1* | 3/2017 | Kuusela ............... A61N 5/1031 |
| 2019/0054320 | A1 | 2/2019 | Owens |
| 2020/0282232 | A1 | 9/2020 | Khuntia |
| 2021/0128946 | A1* | 5/2021 | Smith .................... G16H 50/20 |
| 2021/0393982 | A1 | 12/2021 | Lansonneur |

(Continued)

FOREIGN PATENT DOCUMENTS

| EP | 3682945 B1 * | 3/2021 | ........... A61N 5/1031 |
| EP | 4252838 A1 | 10/2023 | |

(Continued)

OTHER PUBLICATIONS

Folkerts, Michael M. et al.; A Framework for Defining FLASH Dose Rate for Pencil Beam Scanning; Med. Phys. 47 (12), Dec. 2020; pp. 6396-6404.

(Continued)

*Primary Examiner* — Mark R Gaworecki
(74) *Attorney, Agent, or Firm* — Fitch, Even, Tabin & Flannery LLP

(57) ABSTRACT

A control circuit optimizes an energy treatment plan (such as, but not limited to, a Flash energy treatment plan) to therapeutically treat a given patient's treatment volume with energy to provide an optimized energy treatment plan. The control circuit determines at least one delivered dose rate as regards applying the energy pursuant to the optimized energy treatment plan and then determines a quality assurance dose rate metric that corresponds to that at least one delivered dose rate. The control circuit then informs a user regarding information that corresponds to the quality assurance dose rate metric.

17 Claims, 4 Drawing Sheets

(56) References Cited

U.S. PATENT DOCUMENTS

2022/0199221 A1* 6/2022 Khuntia ............... A61N 5/1031
2023/0310889 A1* 10/2023 Lansonneur ......... A61N 5/1031
                                                          378/65

FOREIGN PATENT DOCUMENTS

WO    WO-2018185146 A1 * 10/2018    ........... A61N 5/1031
WO    WO-2022182679 A1 *  9/2022    ............. A61N 5/103

OTHER PUBLICATIONS

Lin, Binwei et al.; FLASH Radiotherapy: History and Future; Frontiers in Oncology; May 2021, vol. 11, Article 644400; 7 pages.
European Search Report from related European Patent Application No. 23216771, dated Apr. 10, 2024; 2 pages.

* cited by examiner

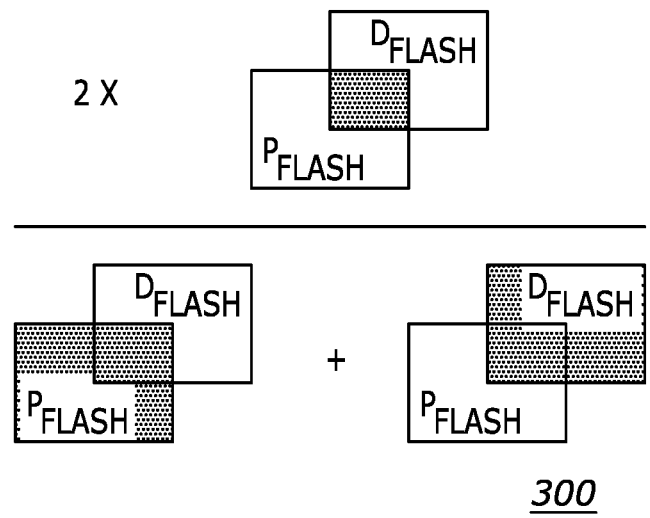
FIG. 3
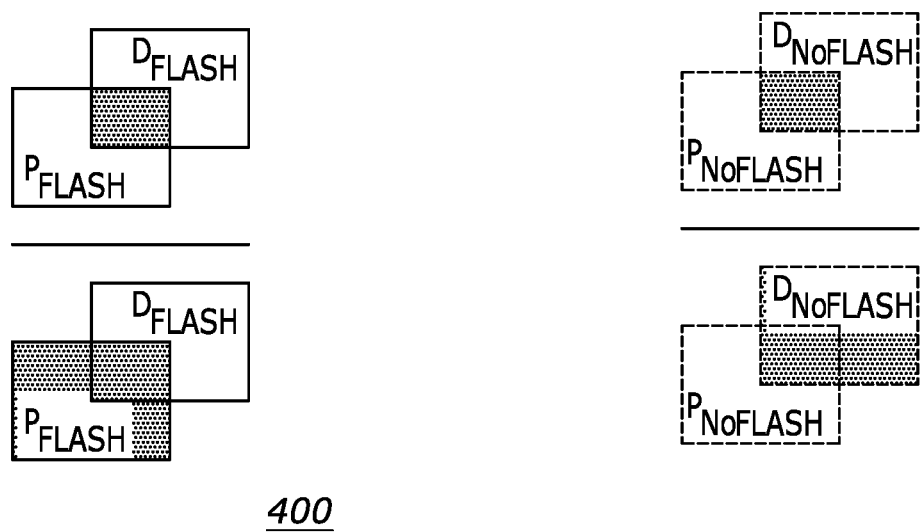
FIG. 4
FIG. 5

ENERGY TREATMENT PLAN QUALITY ASSURANCE DOSE RATE METRIC APPARATUS AND METHOD

TECHNICAL FIELD

These teachings relate generally to treating a patient's planning target volume with energy pursuant to an energy-based treatment plan and more particularly to optimizing an energy-based treatment plan.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to only a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often automatically generated through a so-called optimization process. As used herein, "optimization" will be understood to refer to improving a candidate treatment plan without necessarily ensuring that the optimized result is, in fact, the singular best solution. Such optimization often includes automatically adjusting one or more physical treatment parameters (often while observing one or more corresponding limits in these regards) and mathematically calculating a likely corresponding treatment result (such as a level of dosing) to identify a given set of treatment parameters that represent a good compromise between the desired therapeutic result and avoidance of undesired collateral effects.

Inaccurate dose delivery can result in either insufficient radiation to effect a cure and/or excessive radiation that potentially harms healthy tissue. Quality assurance (QA) tools and protocols are therefore sometimes utilized to verify the efficacy of a given optimized energy treatment plan. Unfortunately, existing QA tools are often inadequate to the task and/or difficult and non-intuitive to employ for all application settings by the responsible technicians. This can be especially true when the treatment plan comprises a so-called Flash energy treatment plan.

BRIEF DESCRIPTION OF THE DRAWINGS

The above needs are at least partially met through provision of the energy treatment plan quality assurance dose rate metric apparatus and method described in the following detailed description, particularly when studied in conjunction with the drawings, wherein:

FIG. 3 comprises a schematic representation as configured in accordance with various embodiments of these teachings;

FIG. 4 comprises a schematic representation as configured in accordance with various embodiments of these teachings;

FIG. 5 comprises a schematic representation as configured in accordance with various embodiments of these teachings;

Figure 1:
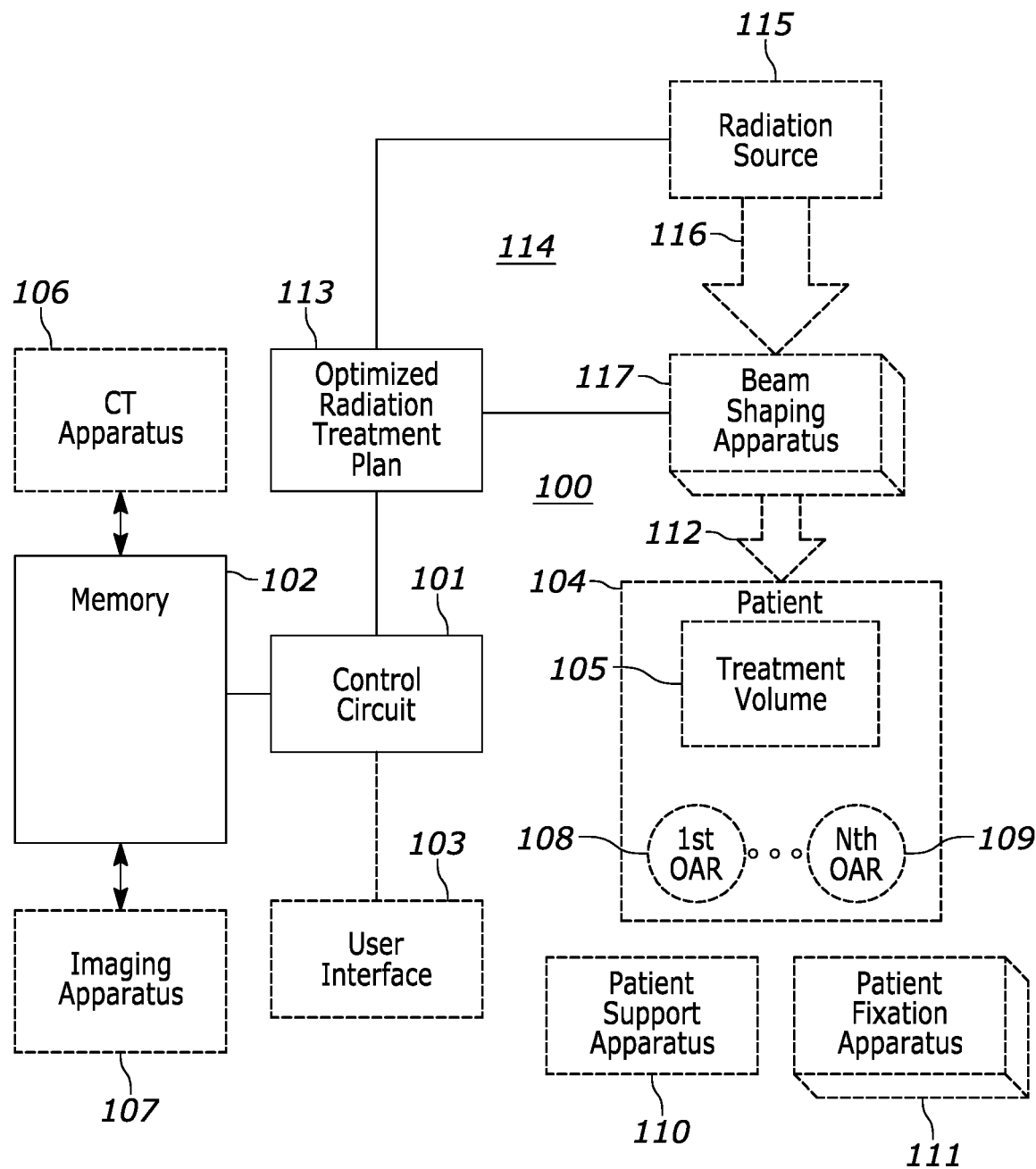
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, pursuant to these various embodiments a control circuit optimizes an energy treatment plan (such as, but not limited to, a Flash energy treatment plan) to therapeutically treat a given patient's treatment volume with energy to provide an optimized energy treatment plan. The control circuit determines at least one delivered dose rate as regards applying the energy pursuant to the optimized energy treatment plan and then determines a quality assurance dose rate metric that corresponds to that at least one delivered dose rate. The control circuit then informs a user regarding information that corresponds to the quality assurance dose rate metric.

These teachings will accommodate a variety of optimized energy treatment plans including, but not limited to, photon treatment plans, electron treatment plans, proton treatment plans, and ion-based treatment plans.

When determining the aforementioned delivered dose rate, these teachings will accommodate determining a delivered dose rate as regards applying the energy pursuant to the optimized energy treatment plan to a non-targeted volume for the given patient.

By one approach, determining the quality assurance dose rate metric can comprise, at least in part, comparing at least one predicted dose rate with the at least one delivered dose rate. By one approach, determining the quality assurance dose rate metric may comprise, at least in part, comparing information that corresponds to the at least one delivered dose rate with at least one threshold value. That threshold value may comprise a plurality of threshold values within a given patient volume (where, for example, at least some of the plurality of threshold values each correspond to a different patient depth).

By one approach, the quality assurance dose rate metric comprises a number. If desired, the quality assurance dose rate metric may consist only of a number.

So configured, these teachings can represent whether a given treatment plan passes a required quality assurance step using only limited and simple to understand metrics. Though relatively simple and intuitive, the quality assurance dose rate metric provided by these teachings can represent with assurance whether regions in which a predicted dose rate were in fact irradiated with at least a minimal dose rate.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as optimization information for a particular patient and information regarding a particular radiation treatment platform as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan (such as, for example, an optimized radiation treatment plan 113). This energy-based treatment plan typically comprises specified values for each of a variety of treatment-platform parameters during each of a plurality of sequential exposure fields. In this case the energy-based treatment plan is generated through an optimization process, examples of which are provided further herein.

By one approach the control circuit 101 can operably couple to an energy-based treatment platform 114 that is configured to deliver therapeutic energy 112 to a corresponding patient 104 in accordance with the optimized energy-based treatment plan 113. The patient 104 may have a treatment volume 105 and one or more organs-at-risk (OAR) as represented by a 1st OAR through an Nth OAR (denoted by the reference numerals 108 and 109). These teachings are generally applicable for use with any of a wide variety of energy-based treatment platforms/apparatuses. In a typical application setting the energy-based treatment platform 114 will include an energy source such as a radiation source 115 of ionizing radiation 116.

By one approach this radiation source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the radiation source 115 along that arcuate pathway, and may accordingly control when the radiation source 115 starts moving, stops moving, accelerates, de-accelerates, and/or a velocity at which the radiation source 115 travels along the arcuate pathway.

As one illustrative example, the radiation source 115 can comprise, for example, a radio-frequency (RF) linear particle accelerator-based (linac-based) x-ray source. A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more energy-shaping apparatuses (for example, beam-shaping apparatuses 117 such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Figure 2:
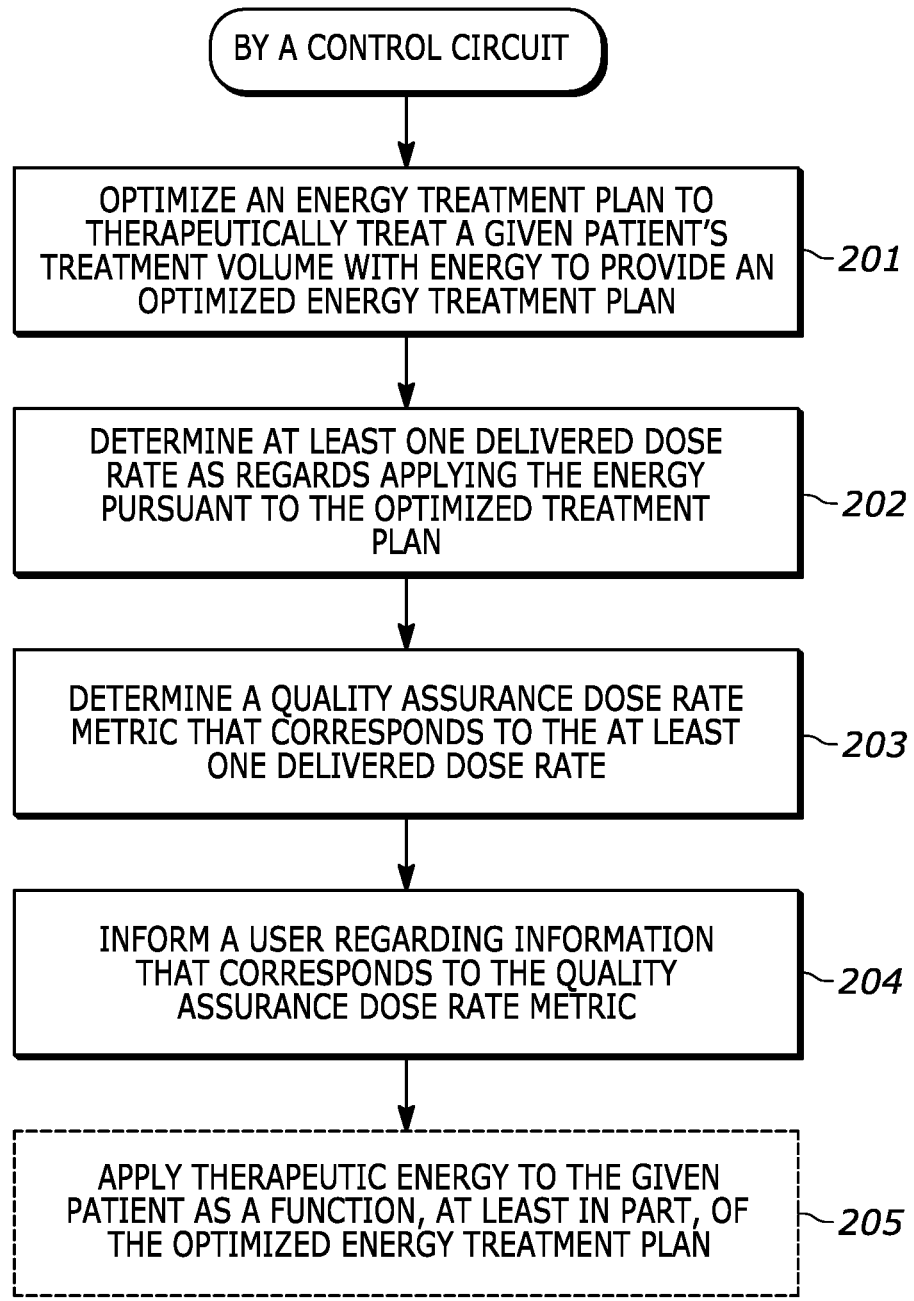
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned control circuit 101) will be described. Generally speaking, this process 200 serves to facilitate generating an optimized radiation treatment plan 113 to thereby facilitate treating a particular patient with therapeutic radiation using a particular radiation treatment platform per that optimized radiation treatment plan.

For the sake of an illustrative example, and without intending to suggest any limitations with respect to these teachings, the following description presumes that the optimized radiation treatment plan comprises a so-called Flash energy treatment plan. Flash energy treatment is a known area of prior art endeavor, albeit a relatively new area of consideration. Flash radiotherapy is a technique (at least for photon, electron, and proton treatments) that employs very brief, very high dose rates (utilizing large beam currents). Flash treatments hold the promise of shortening treatment time to just one to three 1-second sessions while also potentially reducing side effects, perhaps considerably. For example, a significant sparing of normal tissue notwithstanding iso-effective tumor growth delay has been demonstrated through very brief irradiation at dose rates on the order of 40 Gy/s. This sparing of normal tissue has been dubbed the Flash effect.

At block 201, the control circuit 101 optimizes an energy treatment plan to therapeutically treat a given patient's treatment volume with energy to provide an optimized energy treatment plan. This plan may comprise, for example, a photon treatment plan, an electron treatment plan, a proton treatment plan, an ion-based treatment plan (employing, for example, heavy ions such as, but not limited to, carbon ions), and so forth. Continuing with the presumption, for the sake of an illustrative example, that the optimized energy treatment plan comprises an optimized Flash energy treatment plan, it will be presumed as well in this example that the optimized energy treatment plan is a proton treatment plan.

At block 202, the control circuit 101 determines at least one delivered dose rate as regards applying the energy pursuant to the optimized energy treatment plan. By one example, this may comprise, at least in part, determining a delivered dose rate as regards applying the energy pursuant to the optimized energy treatment plan to a non-targeted volume (such as, for example, an organ-at-risk for the given patient).

At block 203, the control circuit 101 determines a quality assurance dose rate metric that corresponds to the foregoing at least one delivered dose rate. The latter may include, at least in part, comparing at least one predicted dose rate with the at least one delivered dose rate. By one approach, determining the quality assurance dose rate metric that corresponds to the at least one delivered dose rate can comprise, at least in part, comparing information that corresponds to the at least one delivered dose rate with at least one threshold value. If desired, these teachings will accommodate a plurality of threshold values within a given patient volume. For example, at least some of this plurality of threshold values can each correspond to a different patient depth. Further details in these regards appear below.

By one approach, this quality assurance dose rate metric comprises a number. This number may comprise, for example, an integer. By another approach, the number may comprise a number having a decimal component. If desired, the quality assurance dose rate metric may include (or consist only of) a non-numeric component such as a textual component, a color component, an icon-based component, and so forth. For many application settings, it will suffice for the quality assurance dose rate metric to consist only of a number.

At block 204, the control circuit 101 facilitates informing a user regarding information that corresponds to the aforementioned quality assurance dose rate metric. This can comprise, for example, displaying part or all of the aforementioned quality assurance dose rate metric on the aforementioned user interface 103. So informed, the user may then approve or disapprove of the optimized energy treatment plan based upon the displayed quality assurance dose rate metric. When this process results in a failure to pass the corresponding quality assurance test, the energy treatment plan can be re-optimized with one or more changed parameters and the preceding steps repeated to again develop a corresponding quality assurance dose rate metric for the reoptimized plan. Presuming the plan proves acceptable, at optional block 205 this process 200 will accommodate applying therapeutic energy to the given patient as a function, at least in part, of the approved optimized energy treatment plan.

Additional details regarding these teachings will now be provided by way of some examples. It will be understood that the specific details of these examples are intended to serve an illustrative purpose and are not to be understood as suggesting any particular limitations with respect to these teachings.

In this example, the dose and dose rate for both the optimized plan (P) and the delivery (D) for each voxel can be calculated or reconstructed. (If desired, some number less than each and every voxel can be so considered. For example, up to 90%, 95%, or 98% of all of the voxels may be so considered.)

By one approach, two main criteria can then be defined. These are the minimal dose contribution below which a voxel is disregarded from further analysis to define the volume of interest, and a threshold dose rate, above which a voxel is considered Flash. Optionally, one can include a dose threshold as a third criterion. In this case, a voxel would have to be both above the dose rate threshold and above the dose threshold to be considered Flash.

Pursuing the foregoing approach, first the numbers of planned and delivered Flash voxels, $P_{Flash}$ and $D_{Flash}$, are counted. If $D_{Flash}$ is greater than a predefined percentage of $P_{Flash}$, for example, 95%, then a first QA check is passed:

$$D_{Flash} \geq 0.95 \cdot P_{Flash}.$$

For a second QA check, the spatial overlap of $D_{Flash}$ and $P_{Flash}$ can be quantified using an index. This index can be calculated using any of a variety of approaches. Depending on the exact definition of this metric, the interpretation of the index may differ. In particular, a "good" value by one definition may be a "bad" value by a different definition.

Some possible examples of index definitions will now be presented. These examples are again intended to serve as illustrative examples and are not intended to suggest any limitations or to suggest that other index definitions are not available.

Dice Coefficient of the Flash Volumes

The dice coefficient is a common measure of similarity of two volumes and can be expressed as follows.

$$i = \frac{2 \cdot |P_{Flash} \cap D_{Flash}|}{|P_{Flash}| + |D_{Flash}|}$$

The foregoing describes twice the number of voxels where the two volumes overlap divided by the sum of the number of voxels of both volumes. When the two volumes are identical, the dice coefficient is equal to 1, whereas it is 0 if the two volumes do not overlap at all. A value of 0<i<1 indicates that the two volumes are not identical, but that there is some overlap. FIG. 3 presents a simple schematic representation 300 of the foregoing.

Tversky Index of the Flash Volumes (With Parameters α=1 and β=0)

The Tversky index is asymmetric, meaning that the two volumes are not interchangeable. This index can be expressed as follows.

$$i = \frac{|P_{Flash} \cap D_{Flash}|}{|P_{Flash}|}$$

In this form, the index describes what percentage of the planned Flash voxels were really delivered as Flash. The approach ignores any voxels that were not planned as Flash, but were nevertheless delivered as Flash. The index is equal to 1 if all planned Flash voxels were delivered as Flash, regardless of any additional delivered Flash voxels. This index is equal to 0 if none of the planned Flash voxels are delivered as Flash. A value of 0<i<1 indicates that some, but not all, of the planned Flash voxels are delivered as Flash. FIG. 4 presents a simple schematic representation 400 of the foregoing.

Tversky Index of the Non-Flash Volumes (With Parameters α=0 and β=1)

This metric is very similar to the previous one, but with a slightly different focus. This index can be expressed as follows.

$$i = \frac{|P_{non-Flash} \cap D_{non-Flash}|}{|D_{non-Flash}|}$$

This index considers all the voxels that do not fulfil the Flash criteria. This index thus describes which fraction of the delivered non-Flash voxels were predicted as non-Flash by the planned dose and dose rate distributions. This index is equal to 1 if all non-Flash voxels were predicted and is equal to 0 if none of them were predicted. A value of 0<i<1 indicates that some, but not all, of the non-Flash voxels were predicted as such. FIG. 5 presents a simple schematic representation 500 of the foregoing.

Table 1 presents a summary of the properties of these three index definitions.

TABLE 1

| Index definition | i = 1 | 0 < i < 1 | i = 0 |
|---|---|---|---|
| 1. Dice | Exactly the planned Flash voxels were delivered as Flash, but none more. | There is some overlap between the planned and delivered Flash voxels. One volume may be completely contained in the other one. | There is no overlap between planned and delivered Flash voxels, or one of those volumes is empty. |
| 2. Tversky (Flash) | All planned Flash voxels were delivered as Flash. Additional voxels may have been delivered as Flash. | Some planned Flash voxels were delivered as Flash. | None of the planned voxels were delivered as Flash. There may be other delivered Flash voxels. |
| 3. Tversky (non-Flash) | All delivered non-Flash voxels were predicted by the plan. Additional voxels may have been predicted as non-Flash, but were delivered as Flash. | Some delivered non-Flash voxels were predicted as non-Flash. | None of the delivered non-Flash voxels were predicted as non-Flash by the plan. Other voxels may have been predicted as non-Flash. |

Figure 6:
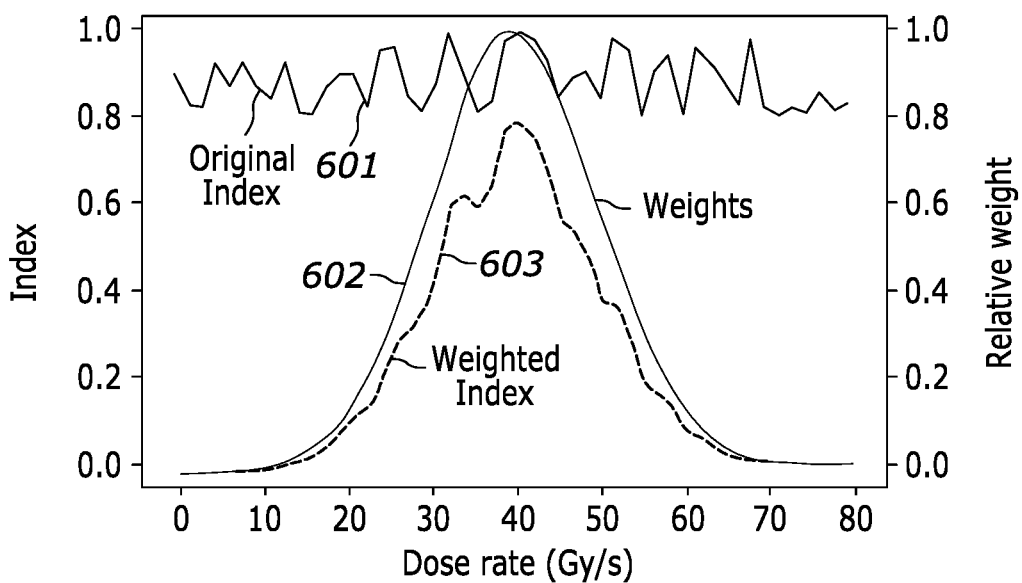
FIG. 6 comprises a graph as configured in accordance with various embodiments of these teachings.

The indexes described above can be calculated for a specific dose rate threshold. Since the biological response to different dose rates may not always be reasonably represented as a step function, and instead the Flash effect may be a smooth function of the dose rate, it may be useful, at least in some application settings, to compare the index for a set of different dose rate thresholds to investigate the dependence. Thus, it might be helpful to consider the index as a function of dose rate threshold graphically, as shown in FIG. 6. More specifically, FIG. 6 depicts an original index 601 that was determined as a function of the dose rate threshold as calculated using one of the above-described definitions. Reference numeral 602 denotes a weighting function w(DR) that reflects the relative importance of each dose rate threshold. And reference numeral 603 denotes a resultant weighted index $i_w$(DR).

To reduce the index for a variable dose rate threshold to a single number, the index as a function of dose rate threshold 601, i(DR) can be integrated within a certain range of dose rate thresholds. The index for varying dose rate threshold may additionally be weighted by the aforementioned weighting function w(DR) 602 using $i_w(DR)=i(DR) \cdot w(DR)$. The final index covering a range of dose rate thresholds can then be calculated as follows.

$$i = \int_{DR_{min}}^{DR_{max}} i_w(DR)dDR,$$

where $DR_{min}$ and $DR_{max}$ define the dose rate threshold range of interest and $i_w(DR)$ is the weighted index as a function of the dose rate threshold. If w(DR) is a constant, all dose rate thresholds are of equal interest. In FIG. 6, dose rate thresholds around 40 Gy/s are considered most important, and dose rate thresholds below 10 Gy/s or above 70 Gy/s are almost entirely disregarded. (It will again be understood that the specifics of this example are intended to serve an illustrative purpose, and that the minimum and maximum dose rate will likely vary based on the situation and/or other indications.)

Figure 7:
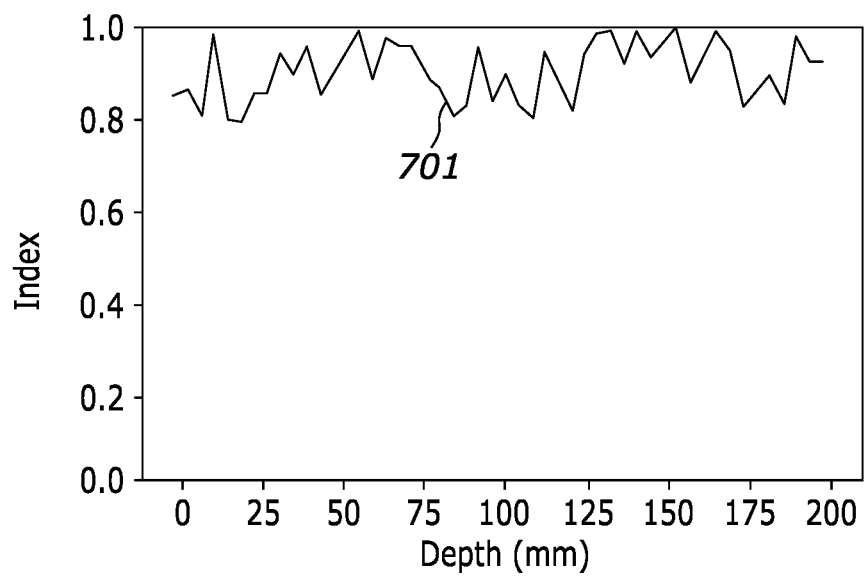
FIG. 7 comprises a graph as configured in accordance with various embodiments of the invention.

The index, regardless of the specific implementation, will usually be calculated for a predefined volume of interest. This volume of interest can, for example, be the entire patient volume or a single two-dimensional slice of voxels at a certain depth. If one is interested in how the index changes along the beam direction, the index can be calculated for each depth slice separately and then represented in a depth-index-diagram. FIG. 7 presents such a graph, where the index 701 is presented as a function of depth along the beam direction (calculated for each two-dimensional slice separately). In this scenario, it usually should not matter how the index is calculated, e.g., whether multiple dose rate thresholds were considered or not.

So configured, these teachings can provide a simple figure of merit that quantifies the overlap of the predicted and the delivered Flash regions. A "bad" figure of merit indicates an unacceptable disagreement between that prediction and the actual delivery. The prescribing physician and/or attending technical specialist can leverage that figure of merit to trigger a reevaluation of the plan before irradiating the patient.

Those skilled in the art will recognize that a wide variety of modifications, alterations, and combinations can be made with respect to the above-described embodiments without departing from the scope of the invention. For example, these teachings can accommodate mixed modality plans such as, for example, combining a Flash proton plan with a conventional volumetric modulated arc therapy (photon) or an intensity modulated proton therapy (proton) plan. In the latter context, the dose levels from the conventional plan can serve as a base or background of sorts for selecting dose thresholds when the Flash part of the plan is considered. Accordingly, it will be understood that such modifications, alterations, and combinations are to be viewed as being within the ambit of the inventive concept.

What is claimed is:

1. A method comprising:
   by a control circuit:
   optimizing an energy treatment plan to therapeutically treat a given patient's treatment volume with energy to provide an optimized Flash energy treatment plan;
   determining at least one delivered dose rate as regards applying the energy pursuant to the optimized energy treatment plan;
   determining a quality assurance dose rate metric that corresponds to the at least one delivered dose rate;
   informing a user regarding information that corresponds to the quality assurance dose rate metric.

2. The method of claim 1 wherein the optimized energy treatment plan comprises one of:
   a photon treatment plan;
   an electron treatment plan;
   a proton treatment plan;
   an ion-based treatment plan.

3. The method of claim 1 wherein determining the at least one delivered dose rate as regards applying the energy pursuant to the optimized energy treatment plan comprises, at least in part, determining a delivered dose rate as regards applying the energy pursuant to the optimized energy treatment plan to a non-targeted volume for the given patient.

4. The method of claim 1 wherein the quality assurance dose rate metric comprises a number.

5. The method of claim 4 wherein the quality assurance dose rate metric consists of a number.

6. The method of claim 1 wherein determining the quality assurance dose rate metric that corresponds to the at least one delivered dose rate comprises, at least in part, comparing information that corresponds to the at least one delivered dose rate with at least one threshold value.

7. The method of claim 6 wherein the at least one threshold value comprises a plurality of threshold values within a given patient volume.

8. The method of claim 7 wherein the at least one threshold value comprises a plurality of threshold values wherein at least some of the plurality of threshold values each correspond to a different patient depth.

9. The method of claim 1 further comprising:
   applying therapeutic energy to the given patient as a function, at least in part, of the optimized energy treatment plan.

10. An apparatus comprising:
    a user interface;
    a control circuit operably coupled to the user interface and configured to:
    optimize an energy treatment plan to therapeutically treat a given patient's treatment volume with energy to provide an optimized Flash energy treatment plan;
    determine at least one delivered dose rate as regards applying the energy pursuant to the optimized energy treatment plan;
    determine a quality assurance dose rate metric that corresponds to the at least one delivered dose rate;
    inform a user, via the user interface, regarding information that corresponds to the quality assurance dose rate metric.

11. The apparatus of claim 10 wherein the optimized energy treatment plan comprises one of:
    a photon treatment plan;
    an electronic treatment plan;
    a proton treatment plan;
    an ion-based treatment plan.

12. The apparatus of claim 10 wherein the control circuit is configured to determine the at least one delivered dose rate as regards applying the energy pursuant to the optimized energy treatment plan by, at least in part, determining a delivered dose rate as regards applying the energy pursuant to the optimized energy treatment plan to a non-targeted volume for the given patient.

13. The apparatus of claim 10 wherein the quality assurance dose rate metric comprises a number.

14. The apparatus of claim 13 wherein the quality assurance dose rate metric consists of a number.

15. The apparatus of claim 10 wherein the control circuit is configured to determine the quality assurance dose rate metric that corresponds to the at least one delivered dose rate by, at least in part, comparing information that corresponds to the at least one delivered dose rate with at least one threshold value.

16. The apparatus of claim 15 wherein the at least one threshold value comprises a plurality of threshold values wherein at least some of the plurality of threshold values each correspond to a different patient depth.

17. The apparatus of claim 10 wherein the control circuit is further configured to:
   apply therapeutic energy to the given patient as a function, at least in part, of the optimized energy treatment plan.

* * * * *